US00PP15140P2

(12) United States Plant Patent
van Rijn

(10) Patent No.: US PP15,140 P2
(45) Date of Patent: Sep. 7, 2004

(54) ANTHURIUM PLANT NAMED '2000-22'

(50) Latin Name: *Anthurium andreanum*
Varietal Denomination: 2000-22

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/722,056

(22) Filed: Nov. 25, 2003

(51) Int. Cl.[7] ..... A01H 5/00
(52) U.S. Cl. ..... Plt./365
(58) Field of Search ..... Plt./365

*Primary Examiner*—Anne Marie Grunberg
(74) *Attorney, Agent, or Firm*—C. A. Whealy

(57) ABSTRACT

A new and distinct cultivar of Anthurium plant named '2000-22', characterized by its upright and outwardly spreading plant habit; freely clumping growth habit; durable dark green leaves; dark red-colored spathes with pale yellow-colored spadices that are positioned slightly above and beyond the foliage on strong and erect scapes; freely flowering habit; and good inflorescence longevity.

2 Drawing Sheets

Botanical classification/cultivar designation: *Anthurium andreanum* cultivar 2000-22.

BACKGROUND OF THE INVENTION

The present invention relates to a new and distinct cultivar of Anthurium plant, botanically shown as *Anthurium andreanum,* and hereinafter referred to by the name '2000-22'.

The new Anthurium is a product of a planned breeding program conducted by the Inventor in Schipluiden, The Netherlands. The objective of the program is to create and develop new compact, freely clumping and freely flowering Anthurium cultivars with strong roots, dark green leaves, attractive spathe color, and good inflorescence longevity.

The new Anthurium originated from a cross by the Inventor on Aug. 7, 1998 of a proprietary selection of *Anthurium andreanum* identified as code number 9701, not patented, as the female, or seed, parent with a proprietary selection of *Anthurium andreanum* identified as code number 9099, not patented, as the male, or pollen, parent. The cultivar 2000-22 was discovered and selected by the Inventor as a flowering plant within the progeny of the stated cross in a controlled environment in Schipluiden, The Netherlands in July, 2000.

Asexual propagation of the new cultivar by meristem culture in a laboratory in Belgium since August, 2000, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 2000-22. These characteristics in combination distinguish '2000-22' as a new and distinct cultivar:

1. Upright and outwardly spreading plant habit.
2. Freely clumping growth habit.
3. Durable dark green leaves.
4. Dark red-colored spathes with pale yellow-colored spadices that are positioned slightly above and beyond the foliage on strong and erect scapes.
5. Freely flowering habit.
6. Good inflorescence longevity.

Plants of the new Anthurium can be compared to plants of the female parent, the proprietary selection identified as code number 9701. In side-by-side comparisons conducted in Schipluiden, The Netherlands, plants of the new Anthurium differed from plants of the selection 9701 in the following characteristics:

1. Plants of the new Anthurium had more durable leaves than plants of the selection 9701.
2. Spathes of plants of the new Anthurium were dark red in color whereas spathes of plants of the selection 9701 were pink in color.

Plants of the new Anthurium can be compared to plants of the male parent, the selection 9099. In side-by-side comparisons conducted in Schipluiden, The Netherlands, plants of the new Anthurium differed from plants of the selection 9099 in plant size as plants of the new Anthurium were smaller than plants of the selection 9099.

Plants of the new Anthurium can be compared to plants of the cultivar Red Queen, disclosed in U.S. Plant Pat. No. 11,813. In side-by-side comparisons conducted in Schipluiden, The Netherlands, plants of the new Anthurium differed from plants of the cultivar Red Queen in the following characteristics:

1. Plants of the new Anthurium had flatter and fleshier leaves than plants of the cultivar Red Queen.
2. Plants of the new Anthurium were more freely flowering than plants of the cultivar Red Queen.
3. Spathes of plants of the new Anthurium were thicker, fleshier and brighter red in color than spathes of plants of the cultivar Red Queen.
4. Plants of the new Anthurium had thicker peduncles than plants of the cultivar Red Queen.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a top perspective view of a typical flowering plant of the cultivar 2000-22.

The photograph on the second sheet comprises a close-up view of typical inflorescences of '2000-22'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe 10-month old plants grown in 14-cm containers in Schipluiden, The Netherlands, in a glass-covered greenhouse with average day temperatures of 23° C., average night temperatures of 21° C. and light levels about 6 kilolux.

Botanical classification: *Anthurium andreanum* cultivar 2000-22.

Parentage:

*Female parent.*—Proprietary selection of *Anthurium andreanum* identified as code number 9701, not patented.

*Male parent.*—Proprietary selection of *Anthurium andreanum* identified as code number 9099, not patented.

Propagation:

*Method.*—By meristem culture.

*Time to initiate roots on a meristem-cultured plant.*—About 28 days at 24° C.

*Time to develop roots on a meristem-cultured plant.*—About 270 days at 20 to 24°C.

*Root description.*—Thick, fleshy, dark pink to cream-colored; lateral roots, thick and abundant.

Plant description:

*Plant shape.*—Upright and outwardly spreading plant habit, inverted triangle and somewhat globular, symmetrical.

*Growth habit.*—Freely clumping, bushy and dense growth habit; about eight clumps per plant. Appropriate for 14-cm containers; moderately vigorous to vigorous.

*Plant height, from soil level to top of leaf plane.*—About 38 cm.

*Plant height, from soil level to top of inflorescences.*—About 46 cm.

*Plant diameter or spread.*—About 67 cm.

*Crop time.*—About ten months are usually required from planting of young plants to finished plants in a 14-cm container.

*Foliage description.*—Arrangement: Alternate; simple. Quantity per plant: About 50. Length: About 22 cm. Width: About 13.8 cm. Shape: Deltoid. Apex: Aristate to apiculate. Base: Cordate. Margin: Entire. Texture, upper and lower surfaces: Leathery; glabrous, smooth; durable. Venation pattern: Pinnate. Color: Developing leaves, upper surface: More green than 146A. Developing leaves, lower surface: 146B. Fully developed leaves, upper surface: Between 147A and 139A. Fully developed leaves, lower surface: 146B. Venation, upper surface: 144A. Venation, lower surface: 144A to 144B. Petiole: Length: About 26.8 cm. Diameter, just below geniculum: About 4 mm. Diameter, at plant base: About 5.5 mm. Texture: Smooth, glabrous. Color: Between 143A and 144A. Geniculum length: About 3 cm. Geniculum diameter: About 5 mm. Geniculum color: 144A to 146B. Wing length: About 3.5 cm. Wing diameter: About 4 mm. Wing color: 146C.

Inflorescence description:

*Inflorescence arrangement.*—Spathes with spadices held slightly above and beyond the foliage. Flowering structures arise from leaf axils. Freely and continuous flowering during the autumn in Schipluiden, The Netherlands. Typically about eight inflorescences per plant. Inflorescences not fragrant.

*Inflorescence longevity.*—Inflorescences last about two months under winter conditions and about three months under summer conditions; inflorescences persistent.

*Spathe.*—Length: About 11.6 cm. Width: About 11.2 cm. Shape: Cordate. Apex: Abruptly acute. Base: Deeply cordate. Margin: Entire. Texture, upper and lower surfaces: Leathery; glabrous, smooth. Aspect: Moderately cupped. Color: When opening, front surface: 46A; towards the basal margins, 45C. When opening, back surface: 47B, towards the basal margins, 48A to 48B. Fully developed, front surface: 45A, towards the basal margins, 45C; color becoming closer to 185B with development. Fully opened, back surface: 46D.

*Spadix.*—Length: About 7.4 cm. Diameter: About 8 mm. Shape: Columnar, tapering towards the apex; apex, obtuse. Cross section: Rounded. Aspect: About 10° from vertical. Color: Immature: 11B; towards the apex, 16A. Mature: 11B; towards the apex, 11A.

*Flowers.*—Quantity per spadix: Numerous, about 500. Shape: Rounded. Height: Less than 0.5 mm. Diameter: About 0.8 mm.

*Reproductive organs.*—Androecium: Anther color: 11D. Amount of pollen: Moderate. Pollen color: 11C. Gynoecium: Stigma shape: Ovoid. Stigma color: N155D. Ovary color: N155D.

*Scape.*—Length: About 35.5 cm. Diameter: About 4 mm. Strength: Strong. Aspect: Erect to slightly outwardly slanted to about 20° from vertical. Color: 144B.

*Seed and fruit.*—Seed and fruit development has not been observed on plants of the new Anthurium.

Disease/pest resistance: Under commercial production conditions, plants of the new Anthurium have not been observed to be resistant to pathogens or pests common to Anthurium.

Temperature tolerance: Plants of the new Anthurium have been observed to tolerate temperatures from about 14 to 36° C.

It is claimed:

1. A new and distinct cultivar of Anthurium plant named '2000-22', as illustrated and described.

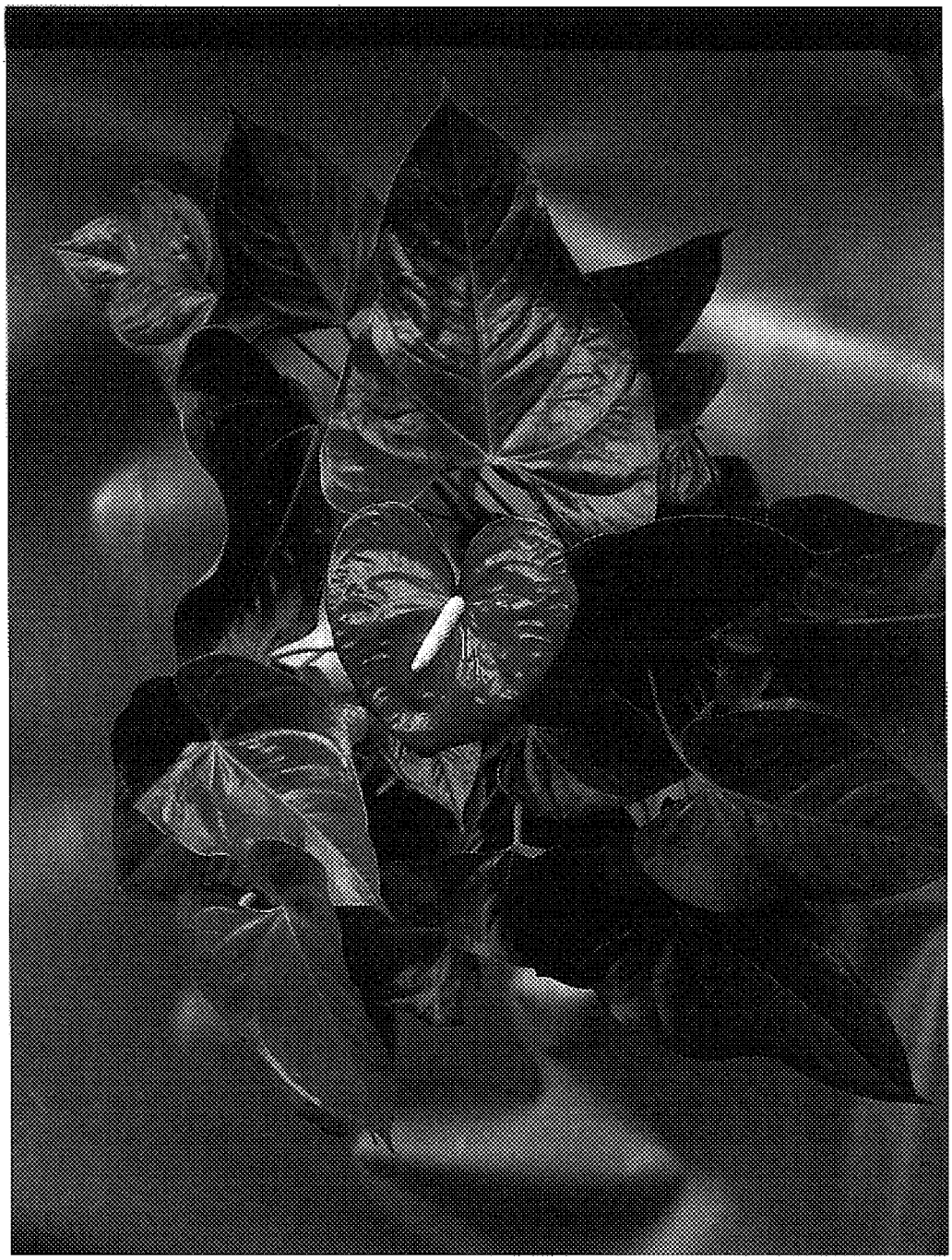

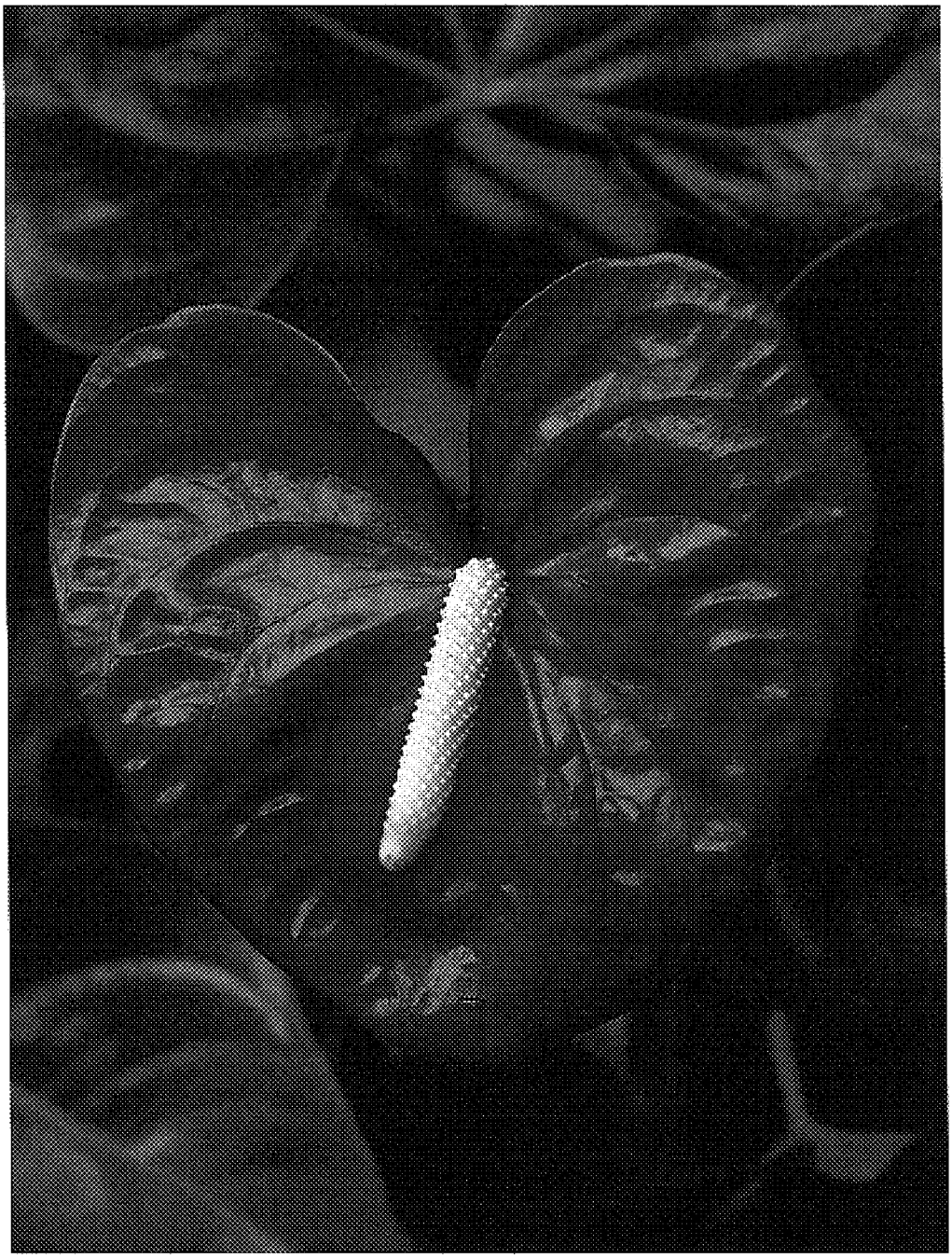

* * * * *